(12) United States Patent
Tominaga et al.

(10) Patent No.: US 6,248,362 B1
(45) Date of Patent: Jun. 19, 2001

(54) LARGE INTESTINAL DELIVERY COMPOSITE

(75) Inventors: Shigeru Tominaga; Toshio Takizawa; Masahiko Yamada, all of Saitama-ken (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/048,252

(22) Filed: Mar. 26, 1998

(30) Foreign Application Priority Data

Mar. 26, 1997 (JP) .................................................... 9-073599

(51) Int. Cl.[7] .................................................... A61K 9/16
(52) U.S. Cl. .......................... 424/490; 424/489; 424/491; 424/494
(58) Field of Search ..................................... 424/490, 486, 424/489, 494, 491

(56) References Cited

U.S. PATENT DOCUMENTS 5,846,565 * 12/1998 Brem et al. ........................... 424/486

FOREIGN PATENT DOCUMENTS

0454383 A1 * 4/1991 (EP) .
0466566 A2 * 7/1991 (EP) .

* cited by examiner

Primary Examiner—Thurman K. Page
Assistant Examiner—William E. Benston, Jr.
(74) Attorney, Agent, or Firm—Wenderoth, Lind & Ponack, L.L.P.

(57) ABSTRACT

A process for delivering the orally administered active ingredients which are safe even in their successive administrations for a long period to the large intestine without elution of the ingredients before reaching the large intestine is disclosed. The process according to the present invention comprises a step of administering orally to animals including human a composite comprising a core containing the active ingredients, an internal layer comprising chitosan with which the core is coated, and an external layer comprising a gastric acid resistant material with which the internal layer is coated, wherein all of the materials in the composite have the empirically established safety to humans. When a material having an iron cation scavenging ability, particularly phytin is used as the active ingredient, it is possible to treat colon cancer efficiently by the process according to the present invention.

24 Claims, 4 Drawing Sheets

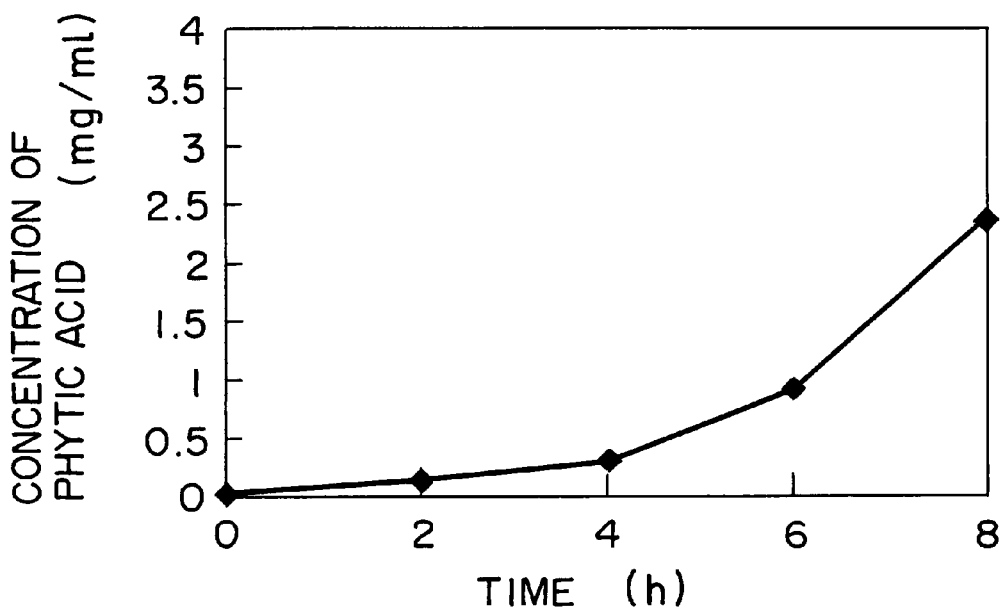
F I G. 1
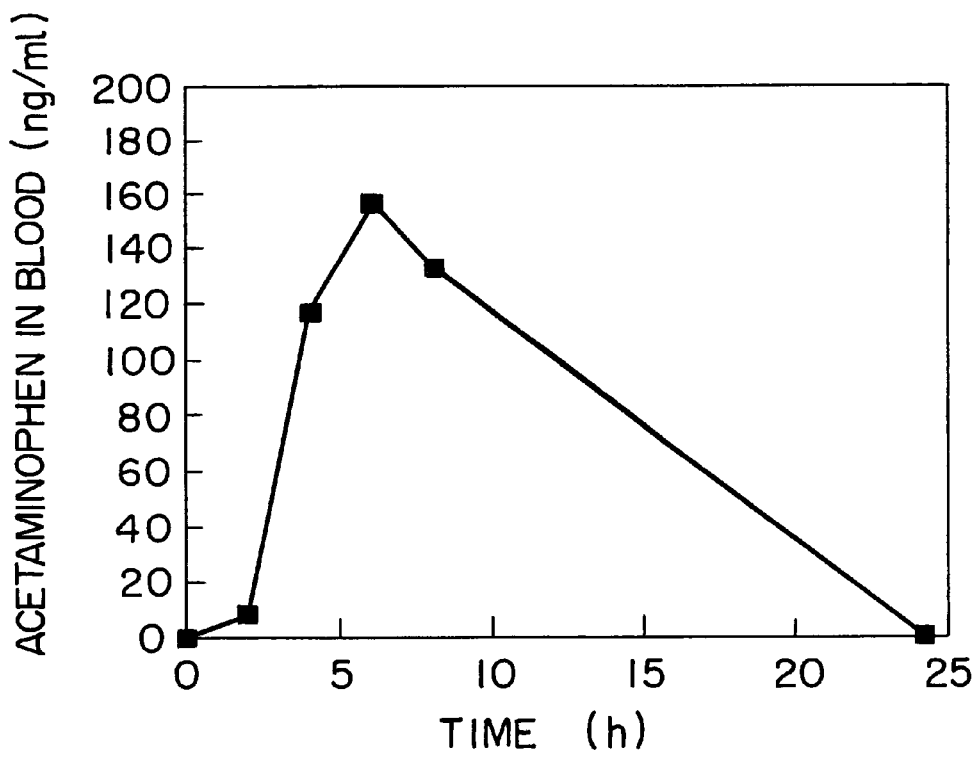
F I G. 2

FIG. 7A  FIG. 7B
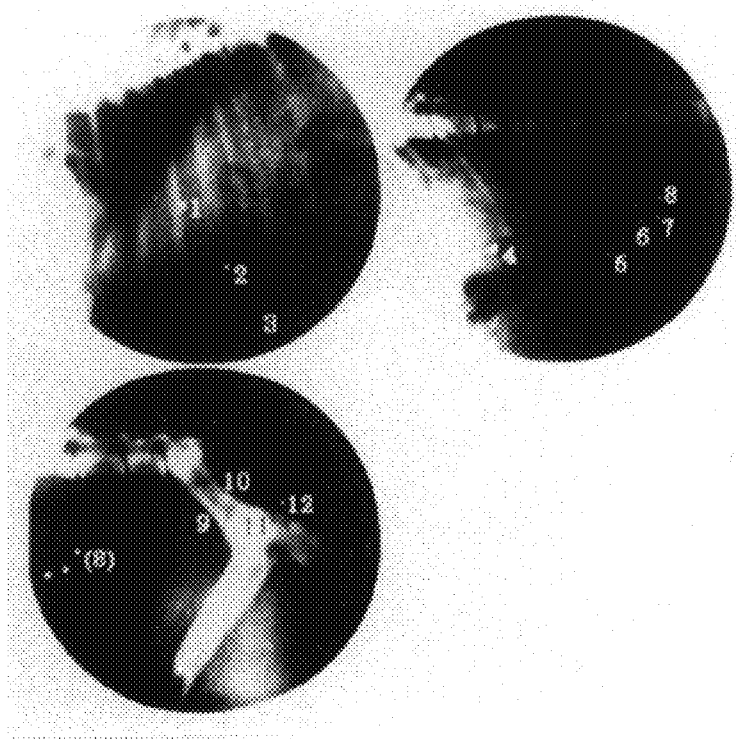
FIG. 7C
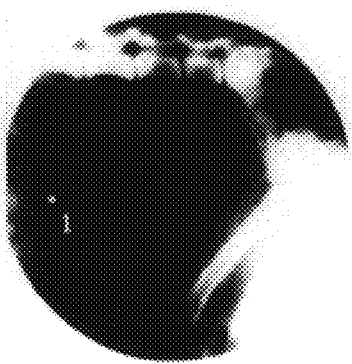
FIG. 8

LARGE INTESTINAL DELIVERY COMPOSITE

BACKGROUND OF THE INVENTION

1. Field of the Invention

The present invention relates to a composite for delivering active ingredients ingested orally to the large intestine without elution of the ingredients from the composite before reaching the large intestine, and a process for delivering the active ingredients with use of the composite.

2. Background Art

Colon cancer is one of the most prevalent cancers in the western countries. Patients of colon cancer has recently been increased also in Japan with the change of eating habits into western style. It is believed that the crisis of colon cancer can be eliminated by dietary care. However, such care actually can be practiced only with difficulty, since it requires expert knowledge and practice over a long period. Moreover, the prophylaxis of colon cancer with medicines or foods requires the lasting administration of them, so that these medicines or foods are also required to have the safety corresponding to or higher than that of ordinary medicines.

In the meantime, the mechanism of occurrence of colon cancer has been gradually elucidated in these years. It is believed as one of the possible mechanism of oncogenesis that lipid peroxide generated by the catalytic action of iron cation in the large intestine results in the damage of genes, which promotes the canceration of cells. It is thus believed essential for the prophylaxis of cells. It is thus believed essential for the prophylaxis of colon cancer to transform the iron cation into an innocuous form.

One of the present inventors has studied numerous materials which have been ingested by human for a long period and has found that phytins occurring in a wide variety of foods and having epidemiologically and cytologically established availability effectively work for transform the iron cation into an innocuous form in the large intestine (Cereal Chemistry, 59(6),525,1982). Intense lipid peroxide suppressive activity of phytins based on the iron cation scavenging ability is the most important activity for the prophylaxis of colon cancer (Molecular Medicine, 33(4), 404 (1996)).

However, phytins are also known to have a mineral ingestion inhibitory effect, and it is indicated that phytins are harmful when ingested in a large amount. Thus, there is a need of a composite which can pass as an innocuous form through the upper part of the small intestine which is major site of absorbing minerals such as iron or calcium and then release phytins at the large intestine that phytins act on and are absorbed in.

There are also the ingredients in addition to phytins which are preferably delivered only to the large intestine, such as Lactobacillus bifidus, anti-oxidants, and peptides.

There have been described various forms of composites which make possible active ingredients to be delivered to the large intestine including for example those in the form of capsule (Japanese Patent Laid-Open Publication Nos. 41422/1992, 225922/1992, 179618/1994, and 327634/1995), those coated with monolayer (Japanese Patent Laid-Open Publication Nos. 368321/1992, and 2701/1995), and those coated with chitosan and a special polymer (Japanese Patent Laid-Open Publication Nos. 34927/1991, 69333/1992, and 217924/1992). However, all of these composites have problems to be solved.

There is still a need of composites which are safe even in their successive administrations for a long period and can deliver the orally administered an active ingredient to the large intestine without elution of the ingredients from the composite before reaching the aimed site.

SUMMARY OF THE INVENTION

The present inventors have found that a composite in which a core containing an active ingredient is coated with an internal layer containing chitosan, and then coated with an external layer comprising a gastric acid resistant material can deliver the active ingredient only to the large intestine, and thus accomplished the invention on the basis of such finding.

Thus, an object of the present invention is to provide a composite which is safe even in their successive administrations for a long period and can deliver the orally administered an active ingredient only to the large intestine without elution of the ingredients from the composite before reaching the large intestine.

Another object of the present invention is to provide a process for delivering an orally administered active ingredient only to the large intestine without elution of the ingredients from the composite before reaching the large intestine.

According to the present invention, there is provided a composite for delivering an active ingredient to the large intestine, and comprises the active ingredient, a core in which the active ingredients are contained, an internal layer comprising chitosan with which the core is coated, and an external layer comprising a gastric acid resistant material with which the internal layer is coated, wherein all of the materials in the composite have the empirically established safety to humans.

Furthermore, according to the present invention, there is provided a process for delivering an active ingredient only to the large intestine of animals, including humans, which comprises a step for administering orally a composite comprising a core in which the active ingredient is contained, an internal layer comprising chitosan with which the core is coated, and an external layer comprising a gastric acid resistant material with which the internal layer is coated to animals, including humans.

According to the present invention, there is provided a composite having a property that an active ingredient is not eluted at the stomach or the small intestine but eluted at the large intestine. Thus, it can deliver the active ingredient to the large intestine as the aimed site without contact of the active ingredients with the stomach or the small intestine.

The gastric acid resistant material of the external layer prevents chitosan from decomposing by gastric acid and the internal layer containing chitosan prevents the elution of the active ingredients in the core in the small intestine. Then, in the large intestine, chitosan is relaxed and decomposed by the invasion of water with the passage of time due to the effect of intestinal microorganisms and osmotic pressure, and thereby it is believed that the active ingredients are for the first time eluted in the large intestine.

Chitosan contained in the internal layer is a material which is compatible and non-toxic to organisms and has already been applied to many foods and cosmetics, and of which safety to humans have been proved. It is possible to obtain a composite which may be administered consecutively for a long period and has an extremely high safety by constituting the core, the ingredients other than chitosan in the internal layer and the external layer with materials have the established safety to humans. This is a major advantage of the present invention.

BRIEF DESCRIPTION OF THE DRAWINGS

FIG. 1 is a graph which illustrates the time-dependent amount of phytic acid eluted from the large intestine-delivering composite according to the present invention in an artificial digestive fluid.

FIG. 2 is a graph which illustrates the time-dependent acetaminophen concentration in blood of beagle dogs having administered the acetaminophen containing large intestine-delivering composite according to the present invention thereto.

FIGS. 3 to 8 are abdominal roentgenogram of a beagle dog having administered the composite according to the present invention thereto.

FIG. 3 is a roentgenogram of the stomach, the small intestine and the upper part of the large intestine immediately after the administration of the composite.

FIG. 7A is a roentgenogram of the stomach, the small intestine and the upper part of the large intestine, FIG. 7B is of the small intestine and the upper part and lower part of the large intestine and FIG. 7C is of the lower part of the large intestine eight hours after the administration of the composite, and FIG. 8 is a roentgenogram of the lower part of the large intestine 24 hours after the administration of the composite.

DETAILED DESCRIPTION OF THE INVENTION

Definition

Figure 3:
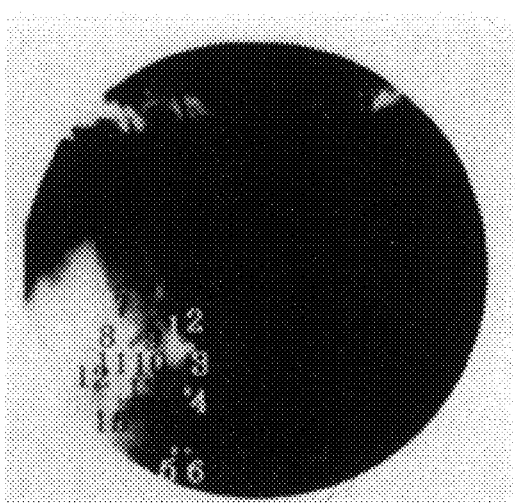
Figures 4A, 4B:
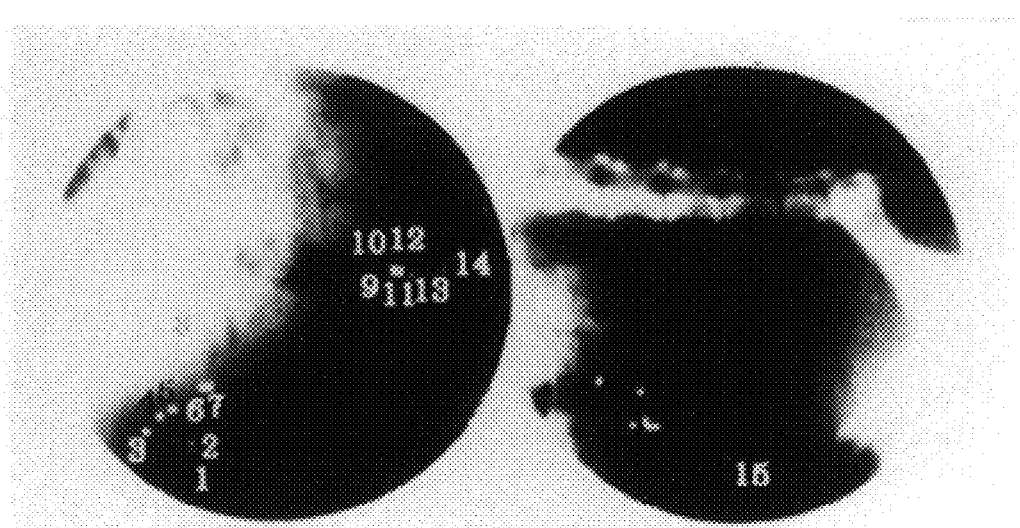
FIG. 4A is a roentgenogram of the stomach, the small intestine and the upper part of the large intestine
FIG. 4B is of the small intestine and the upper part and lower part of the large intestine two hours after the administration of the composite.
Figures 5A, 5B:
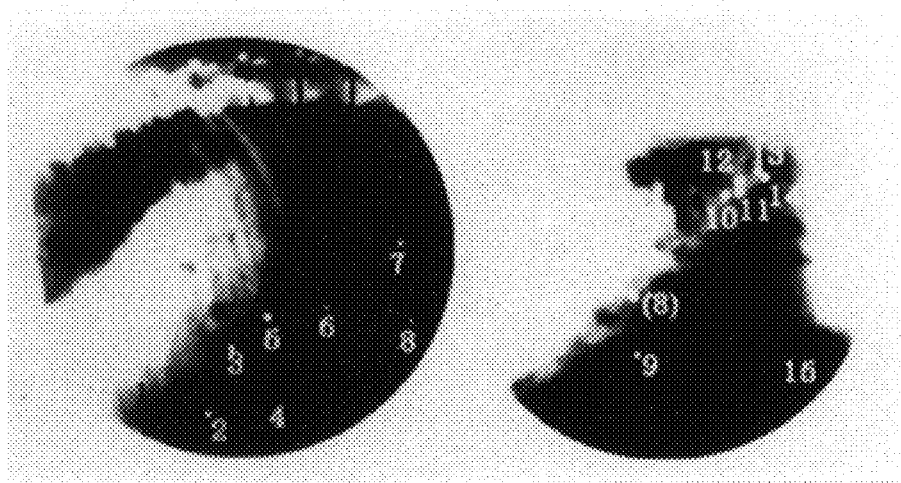
FIG. 5A is a roentgenogram of the stomach, the small intestine and the upper part of the large intestine
FIG. 5B is of the small intestine and the upper part and lower part of the large intestine four hours after the administration of the composite.
Figures 6A, 6B:
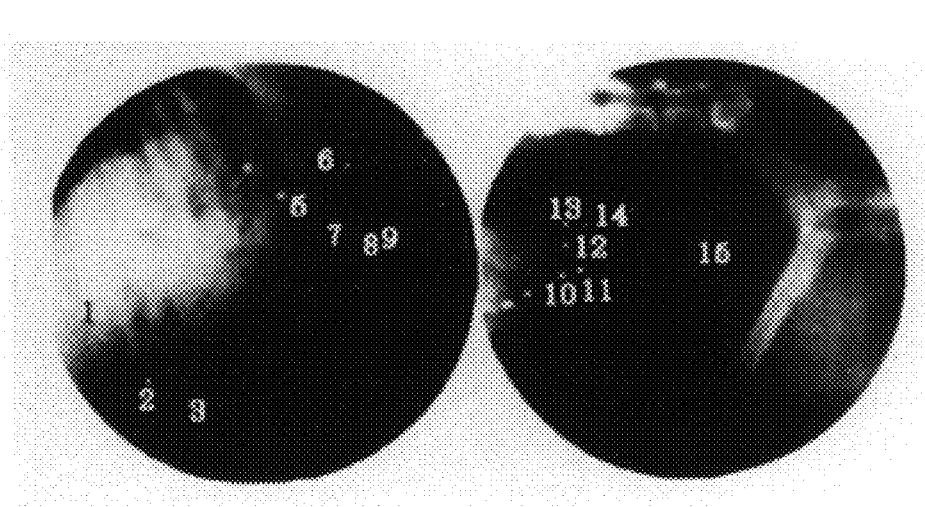
FIG. 6A is a roentgenogram of the stomach, the small intestine and the upper part of the large intestine
FIG. 6B is of the small intestine and the upper part and lower part of the large intestine six hours after the administration of the composite.

The term "materials having the empirically established safety to humans" means herein, for example, a "food" or "food additive." The term "food" or "food additive" is exemplified by but not limited to the materials of which use is permitted by Japanese regulations relating to foods and food additives, for example, the Japanese Food Sanitation Law. The term "food" or "food additive" which is also intended to encompass foods and food additives which are recognized in other countries outside Japan, even if not recognized under the Japanese regulations.

Composite

Active ingredients and cores, and processes for preparing them

Active ingredients contained in the core of the composite according to the present invention include those which is preferably delivered directly to the large intestine. Such active ingredients may be either solid or liquid. These ingredients is preferably those of which safety to humans have been confirmed, particularly foods and food additives, but not limited thereto.

The ingredients which are desirably delivered directly to the large intestine include iron cation scavengers, particularly phytins for the therapy or prophylaxis of colon cancer. As described above, phytins is likely to inhibit the absorption of minerals in small intestine. According to the composite of the present invention, it is possible to deliver the phytins solely to the large intestine where the phytins are released but not released in small intestine. The composite according to the present invention comprising phytins as the active ingredients is useful for the prophylaxis of colon cancer. The prophylactics of colon cancer comprising phytins as the active ingredients are described in details below.

Further preferred active ingredients include Lactobacillus bifidus, anti-oxidants, and peptides. Further, two or more of them may be used in combination.

The core may comprise the active ingredients solely or the active ingredients together with other excipients. Such excipients are preferably the materials of which safety to humans has been confirmed, particularly foods and food additives. Such excipients include sugar, starch, cellulose and lactose. Specifically, when the active ingredients or active ingredient containing concentrates are liquid, cellulose or lactose is preferably used.

In addition, the core may comprises the other ingredients, which include an antioxidant such as vitamin C and vitamin E and a agent for inhibiting an activity of water such as starch and nistose. These ingredients are preferably the materials of which safety to humans has been confirmed, particularly foods and food additives.

The core is preferably in the form of granulates, and granulation may be carried out by a method conventionally used in the art. The size of the core may be appropriately determined, and preferably in the range of 1–10 nm.

The amounts of the active ingredients in the core, that is the amounts of the excipients and the other ingredients are not specifically limited, but the amounts are preferably 10% by weight or more, desirably in the range of 30–95% by weight when the active ingredients are phytins.

Internal layer and process for preparing it

The internal layer of the composite according to the present invention comprises chitosan. Chitosan is a deacetylation product of chitin with a concentrated alkali solution, β-1,4-poly-D-glucosamine. The molecular weight of chitosan is not specifically limited, but is preferably in the range of about 10,000 to 1,000,000, more preferably in the range of about 100,000 to 500,000. Furthermore, the degree of deacetylation is preferably in the range of about 30 to 100%, more preferably in the range of about 65 to 95%, The internal layer may comprise a chitosan film which is formed buy coating the surface of the core with a chitosan solution. Chitosan may be dissolved in a dilute acid solution (preferably organic acids such as acetic acid, citric acid, or malic acid) to form a 1—about 10% chitosan solution, which is sprayed on the surface of the core and dried to form a chitsosan film. This procedure may be carried out by a coating technique well-known in the art with a film coating machine or the like.

According to the preferred embodiment of the present invention, the chitosan solution described above may comprise the other ingredients such as a water proofing agent in order to increase the water resistance of the internal layer. There can be added water proofing agents such as glycerol, propylene glycol, or sugar esters which are known as a plasticizer. According to another preferred embodiment of the present invention, there can be also added food fibers such as wheat bran and corn fiber as a water resistant ingredient in an amount of 20–200% by weight to chitosan.

The thickness of the internal layer may be appropriately determined, and it is preferably in the range of 1—about 1,000 μm, more preferably 100–300 μm.

External layer and process for preparing it

The composite according to the present invention comprises an external layer comprising a gastric acid resistance material on the internal layer. The gastric acid resistant material may be any material in the art provided it is a film material which can protect the content from the environments in the stomach. In other words, a film forming material which has proteolysis in the small intestine and acid resistance in the stomach. It is preferably a material of which safety to humans has been confirmed, particularly foods and food additives. Specifically, it is preferably an antioxidant or a material used as a coating material for foods such as a enteric coating.

The preferred examples of such gastric acid resistant materials include prolamine proteins, such as wheat gliadin and zein, and oils and fats, among which, zein is employed most preferably from the viewpoint of film strength and availability. Zein is known a water-insoluable protein which is present primarily in the endosperm of corn, rich in proline and glutamic acid but free of tryptophan and lysine.

The external layer may be formed by coating the surface of the internal layer with a solution of the gastric acid resistant material and drying the solution to form a film. By way of example, when zein is employed as the gastric acid resistant material, zein may be dissolved in ethanol to form a 1–15% solution, which is treated in the same manner as in the case of the internal layer.

Furthermore, there can be added a water proofing agent as a film forming aid in order to increase the water resistance of the external layer.

The thickness of the external layer may be appropriately determined, and it is preferably in the range of 5–about 300 $\mu$m, more preferably 10–about 50 $\mu$m.

The composite according to the present invention is primarily in the form of granule, but the form is not limited thereto unless the effect according to the present invention is excessively decreased. It is also possible if necessary, to use a combination of coloring, drageé forming treatment, and/or the use of the composite as a constituent of an other composite.

Process for delivering the active ingredients to the large intestine/prophylaxis of colon cancer The composite according to the present invention can deliver selectively the active ingredients to the large intestine solely. Thus, according to the present invention, there is provided a process for delivering the active ingredients to the large intestine solely.

Furthermore, when an iron cation scavenger, particularly phytins is used as an active ingredient, the composite according to the present invention is useful for a prophylactic of colon cancer. Thus, according to the present invention, there is provided a prophylactic for colon cancer. Also, from the other viewpoint, there is provided a process for preventing colon cancer, which comprises a step of administering the prophylactic orally.

The term phytins herein means phytic acid and salt thereof, and phytic acid having a structure in which inositol is linked to phosphoric acid is a chelating agent as strong as EDTA. The phosphate group is linked to inositol in an amount of 4–6 residues, and the chelating ability increases along with the increase of the residues. In particular, the phytin acid includes inositol 6-phosphate and a metal salt thereof, inositol 5-phosphate and a metal salt thereof, inositol 4-phosphate and a metal salt thereof, and a concentrate these compounds in a concentration of 10% by weight or more. For instance, phytin (calcium-magnesium salt of inositol 6-phosphate) and phytic acid correspond to this category. In this connection, when the number of the phosphate residues is 3 or less or the concentrate contains the compound only in a concentration of less than 10% by weight, satisfactory effects of the phytic acids may not be expected due to the low chelating ability, but the use of these phytic acids is also included in the present invention.

A proposed daily dosage of the composite according to the present invention for preventing colon cancer is 1 to 1000 mg in terms of phytins.

Furthermore, the phytins are known useful for the therapy of colon cancer as well as the prophylaxis and therapy of prostatic cancer, breast cancer and liver cancer. Thus, according to the present invention, there are provided a therapeutic agent of colon cancer as well as prophylactic and therapeutic agents of prostatic cancer, breast cancer and liver cancer. In addition, according to the present invention, there are provided a process for treating colon cancer as well as the processes for preventing and treating prostatic cancer, breast cancer and liver cancer.

EXAMPLES

The present invention is now described specifically with reference to examples, but it is not intended to be limited thereto.

Example 1

(1) Preparation composite

Cellulose and phytic acid were sprayed and adhered on a nucleus containing cellulose and lactose while drying the mixture to form granule containing 40% by weight of phytic acid and having a diameter of 4.7 mm. On 400 g of the granule was sprayed 1400 g of a 3.5% by weight chitosan aqueous solution containing 0.8% of glycerol as a plasticizing agent, which was dried to give granule comprising a chitosan layer (internal layer) in a thickness of about 130 $\mu$m on the surface. Then, a solution of 5.9% by weight of zein containing 0.8% of glycerol as a plasticizing agent dissolved in a 80% ethanolic aqueous solution was prepared, and a 350 g portion of the resulting solution was sprayed on 300 g of the granule and dried to form a zein layer (external layer) having a thickness of 45 $\mu$m.

(2) Evaluation test

The composite prepared as above was shaken lightly at a speed of 1 reciprocation/sec in an artificial digesting fluid, and the concentration of phytic acid in the artificial digesting fluid was measured. As the artificial digesting fluid was used the artificial gastric juice A (a solution of 16% by weight of pepsin (WAKO PURE CHEMICAL INDUSTRIES, LTD.) in Japanese Pharmacopoeia solution 1) for 2 hours after starting the test, and the artificial intestinal juice B (a solution of 0.1% by weight of trypsin (SIGMA, Type III from Bovine Pancreas) and 0.1% by weight of chymotripsin (SIGMA, Type II from Bovine Pancreas) in Japanese Pharmacopoeia solution 2) on and after 2 hours.

The results are shown in FIG. 1. Elution of phytic acid started after 6 hours, and the concentration of the phytic acid eluted was increased further after 8 hours, which corresponded to the time that the composite has passed through small intestine and reached the large intestine in the gastrointestinal tract of human, and suggested that the composite has disintegrating property in the large intestine.

Example 2

(1) Preparation of composite

A composite was prepared by the following method in accordance with Example 1. On a nucleus containing cellulose and lactose was sprayed acetaminophenon, followed by cellulose and phytic acid on the outer layer to prepare granule containing 40% by weight of acetaminophen and having a diameter of 4.7 mm. Acetaminophen was used for measuring the transfer of the water-soluble ingredient of the core in the granule at a high sensitivity. Also, phytic acid was used for preventing the direct contact of acetaminophen with chitosan resulting in the change of state of chitosan coated. In addition, acetaminophen was replaced with barium sulfate to prepare granule containing 27% by weight of barium sulfate and having a diameter of 4.7 mm. Furthermore, the granule was coated with a film of chitosan and zein in the same manner as in Example 1.

(2) Evaluation test

After fifteen granules of the composites prepared as above were administered respectively to a beagle dog having a weight of 13.8 kg, the concentrations of the acetaminophen in blood of beagle dogs were measured and roentgenography at abdominal part was conducted. Roentgenograms were of stomach, the small intestine, the upper part of the large intestine and the lower part of the large intestine, which have been photographed at the times immediately after administration, and 2, 4, 6 and 8 hours after administration.

The concentrations of acetaminophen in blood is shown in FIG. 2. Also, roentgenograms are illustrated in FIG. 3.

At the time of 4–6 hour after starting the test, when the composites could be confirmed to have first reached the large intestine, the concentration of acetaminophen in blood was extensively increased as illustrated in FIG. 2, indicating the transfer of the content of the core into blood.

What is claimed is:

1. A composite for delivering an active ingredient to the large intestine, said composite comprising
    a core comprising the active ingredient,
    an internal layer which is coated on said core comprising chitosan, and
    an external layer coated on said internal layer comprising zein.

2. The composite according to claim 1, wherein the active ingredient is a material having an iron cation scavenging ability.

3. The composite according to claim 2, wherein the material having an iron cation scavenging ability is phytin.

4. The composite according to claim 1, wherein the internal and/or external layer further comprise a water proofing agent.

5. The composite according to claim 4, wherein the internal layer comprises a food fiber as a water proofing agent.

6. The composite according to claim 1, wherein the internal layer has a thickness of 1–1,000 µm, and the external layer has a thickness of 5–300 µm.

7. The composite according to claim 1, wherein all of the materials in the composite have an empirically established safety to humans.

8. The composite according to claim 7, wherein all of the materials in the composite are foods and/or food additives.

9. A process for delivering an active ingredient only to the large intestine of an animal, said process comprising
    administering orally to said animal a composite comprising
    a core comprising the active ingredient,
    an internal layer which is coated on said core comprising chitosan, and
    an external layer coated on said internal layer comprising zein.

10. The process according to claim 9, wherein the active ingredient is a material having an iron cation scavenging ability.

11. The process according to claim 9, wherein the internal layer and/or external layer of the composite comprises further a water proofing agent.

12. The process according to claim 11, wherein the internal layer of the composite comprises a food fiber as the water proofing agent.

13. The process according to claim 9, wherein the internal layer of the composite has a thickness of 1–1,000 µm, and the external layer has a thickness of 5–300 µm.

14. The process according to claim 9, wherein all of the materials in the composite have the empirically established safety to humans.

15. The process according to claim 14, wherein all of the materials in the composite are foods and/or food additives.

16. The process according to claim 1, wherein the active ingredient having the iron cation scavenging ability is phytin.

17. The process according to claim 10, wherein the active ingredient is a material having an iron cation scavenging ability is phytin.

18. The process of claim 9, wherein said animal is a human.

19. A process for treating colon cancer in animals comprising
    administering to said animal in need of such treatment a composite comprising
    a core comprising the active ingredient having an iron cation scavenging ability,
    an internal layer which is coated on said comprising chitosan, and
    an external layer coated on said internal layer comprising zein.

20. The process of claim 19, wherein said animal is a human.

21. A process for treating prostatic cancer, breast cancer or liver cancer in an animal, said process comprising administering to said animal in need of such treatment a composite comprising
    a core comprising phytin,
    an internal layer which is coated on said core comprising chitosan, and
    an external layer coated on said internal layer comprising zein.

22. The process of claim 21, wherein said animal is a human.

23. The process of claim 19, wherein all of the materials in the composite have an empirically established safety to humans.

24. The process of claim 21, wherein all of the materials in the composite have an empirically established safety to humans.

* * * * *